United States Patent [19]

Straith

[11] 4,385,628
[45] May 31, 1983

[54] SURGICAL INSTRUMENT

[76] Inventor: Richard E. Straith, 625 Hillcrest Drive, Bloomfield Hills, Mich. 48013

[21] Appl. No.: 349,778

[22] Filed: Feb. 18, 1982

Related U.S. Application Data

[63] Continuation of Ser. No. 142,410, Apr. 21, 1980, abandoned.

[51] Int. Cl.$^3$ .................... A61B 17/28; A61F 5/08
[52] U.S. Cl. .................... 128/92 EA; 128/321; 7/132
[58] Field of Search .................... 128/321, 305, 92 E, 128/92 EA, 92 EC, 92 G, 303 R, 312; 7/129, 132, 137, 130, 125; 30/168; 144/202; 145/24, 25; 433/4, 159; 81/418, 420

[56] References Cited

U.S. PATENT DOCUMENTS 2,698,483  1/1955  Berkowitz .................... 128/321 X
3,946,453  3/1976  Torres .................... 81/418 X

FOREIGN PATENT DOCUMENTS 215410  7/1968  U.S.S.R. .................... 128/312
283501  12/1970  U.S.S.R. .................... 128/92 EA

OTHER PUBLICATIONS

Sklar Surgical Instruments Catalog (1973) p. 222.

*Primary Examiner*—Michael H. Thaler
*Attorney, Agent, or Firm*—Harness, Dickey & Pierce

[57] ABSTRACT

The disclosure relates generally to aesthetic rhinoplasty and more particularly to an instrument and technique for fracturing the lateral walls of the bony vault of the nose in a precise manner without tearing the periosteal attachments in the region of the nasion or double fracturing of the lateral walls of the bony vault.

5 Claims, 10 Drawing Figures

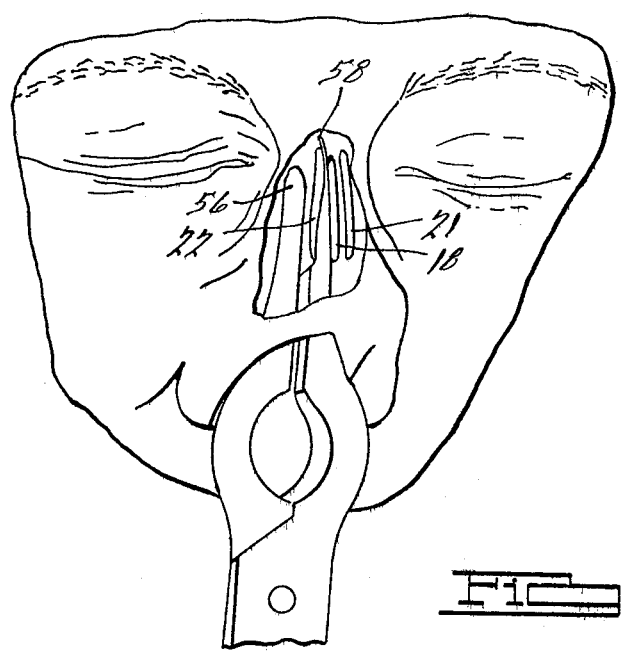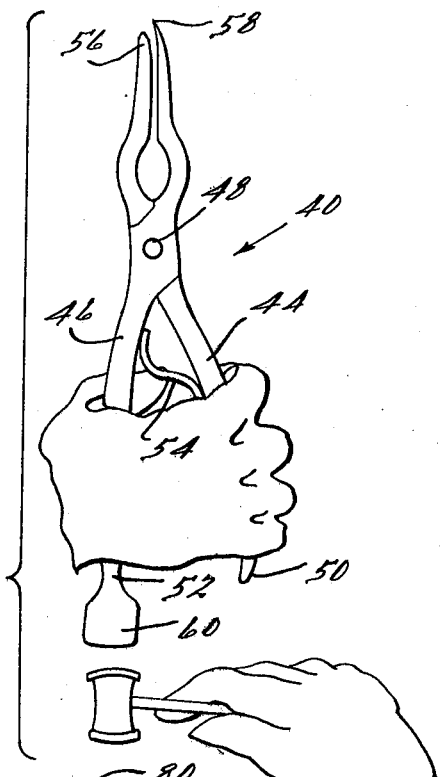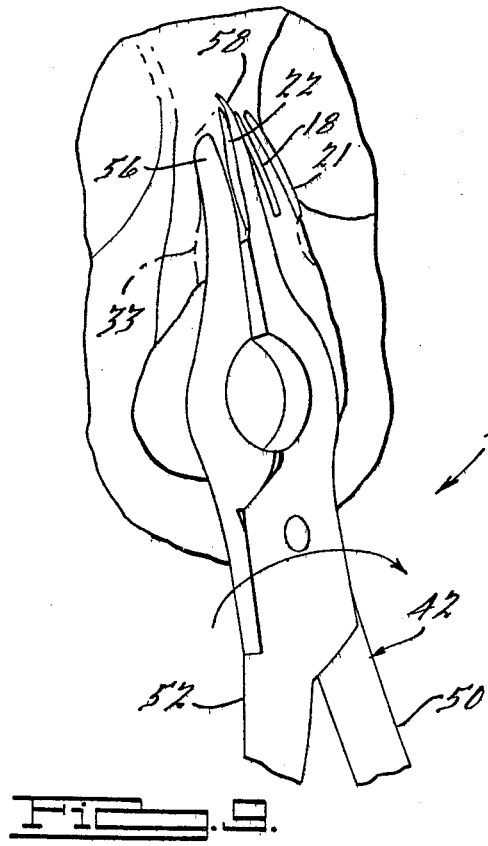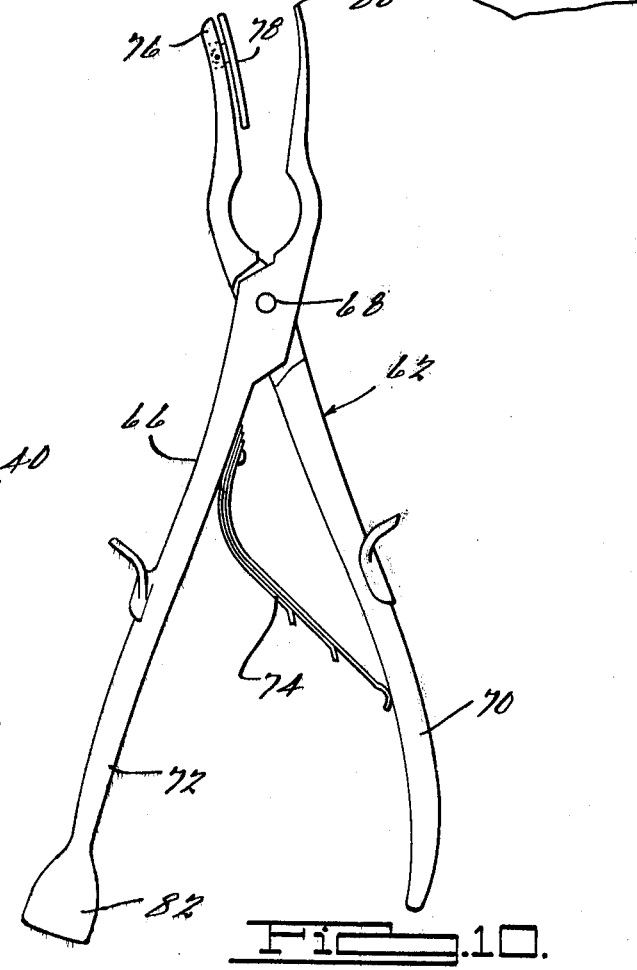

SURGICAL INSTRUMENT

This is a continuation of application Ser. No. 142,410, filed Apr. 21, 1980, now abandoned.

SUMMARY OF THE INVENTION

The invention relates to an improved surgical instrument for fracturing a segment of the bony vault of the nose between the lateral osteotomy and the resected dorsum incident to aesthetic rhinoplasty.

STATEMENT OF THE PRIOR ART

The following patents represent the most pertinent art known to the applicant.

Berkowitz U.S. Pat. No. 2,698,483, issued Jan. 4, 1955, shows a pliers-type of dental clamp having a pair of coactive jaws one of which is fixed and the other of which is pivoted. However, the jaws are arranged almost at right angles with respect to the handles of the clamp, the jaws are not formed so that they can be inserted lengthwise and parallel to the nasal bone at opposite sides thereof, and neither jaw is formed with a chisel edge of sufficient sharpness so that it can be driven into the nasion to a point slightly above a proposed fracture line in a rhinoplasty operation. In short, the patented device is neither intended nor suited for the same purpose as the forceps of this invention.

The Russian Pat. No. 283,501 dated Dec., 1970, shows a pliers-like bone holder and the Russian Pat. No. 215,410 dated July, 1968, shows a pliers-like instrument adapted for use in a type of surgery entirely different than the rhinoplasty surgery for which the forceps of the present invention are particularly adapted for use. As in the case of Berkowitz, the two patented instruments disclosed in the Russian patents have coactive jaws that are heavy and massive in form so as to be incapable of insertion lengthwise and at opposite sides of the nasal bone in a rhinoplasty operation. Moreover, neither jaw is formed with a chisel edge that can be driven into the nasion to a point slightly above a proposed infracture line as is essential to the forceps of this invention.

The Sklar Surgical Instruments Catalog (1973), page 222, shows a finely pointed scissors intended and adapted for use in eye surgery but entirely unsuited for the rhinoplasty operation hereinafter described and for which the forceps of this invention is intended and particularly adapted for use.

DESCRIPTION OF THE DRAWINGS

FIG. 7 is a view of the surgical instrument of the instant invention.

FIG. 8 is a view showing the instrument in position prior to fracture of the cephalic segment.

FIG. 9 is a view similar to FIG. 8 after fracture of the cephalic segment.

FIG. 10 is a view of a modified surgical instrument.

DESCRIPTION OF THE PREFERRED EMBODIMENT

Figure 6:
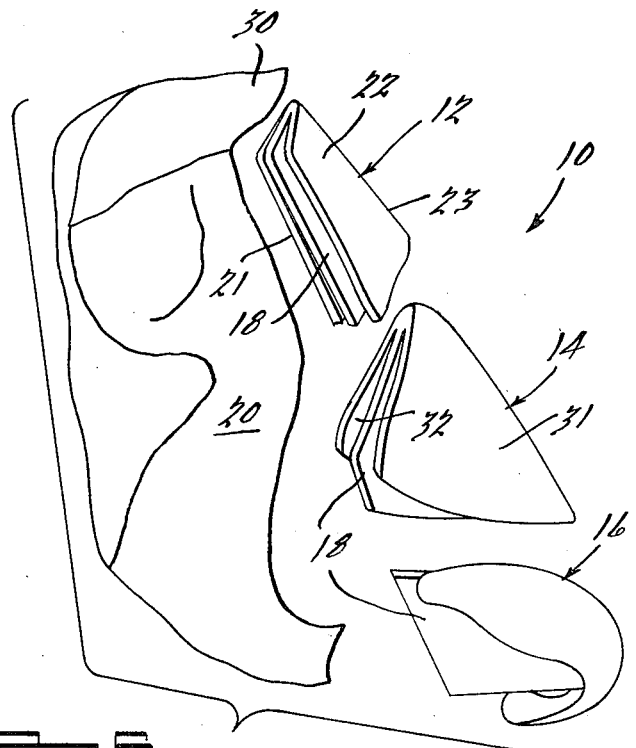
FIG. 6 is a perspective view of the three basic compartments of the nose.

As best seen in FIG. 6, the human nose 10 is essentially a pyramid that is divided into three compartments, namely, the bony vault 12, the upper cartilaginous vault 14, and the lower cartilaginous vault 16. The vaults 12, 14 and 16 have a common supporting partition, the bony and cartilaginous septum 18.

The bony vault 12 forms the principal structural base for the nose 10. It is made up of upward projections of the frontal process of the maxilla 20, from which a pair of nasal bones 21 and 22 extend to form an arch at the union thereof. The posterior border of the bony vault 12 is continuous with the maxilla 20. If the nose 10 is thought of as being cantilevered, the bony vault 12 forms a stable base, with its arch an extension of the skull. Stated in another manner, the bony vault 12, with its cantilevered upper cartilaginous vault 14, fuses with the dorsal edge 23 of the septum 18 to form a structural "I beam" extending from the radix 30 of the skull to the lower cartilaginous vault 16.

The upper cartilaginous vault 14 is made up of paired, triangular cartilages 31 and 32 that extend from the bony vault 12 as a cantilever and are attached along the dorsal border of the septum by a dense fibrous union. The cartilages 31 and 32 are attached to the undersurface of the lateral walls of the bony vault 12 by a membrane. The dorsal segment 23 or upper edge of the upper cartilaginous vault 14 is the bridge that connects the two upper lateral cartilages 31 and 32 to give them stability.

The lower cartilaginous vault 16 forms the base of the nose 10 and is made up of tissues caudal to the free edge of the upper lateral cartilages 31 and 32. Although the lower vault 16 is relatively independent of the vaults 12 and 14, it shares with them the dorsal edge 23 of the septum 18 and the connective tissue attachments to the upper lateral cartilages 31 and 32.

Figure 1:
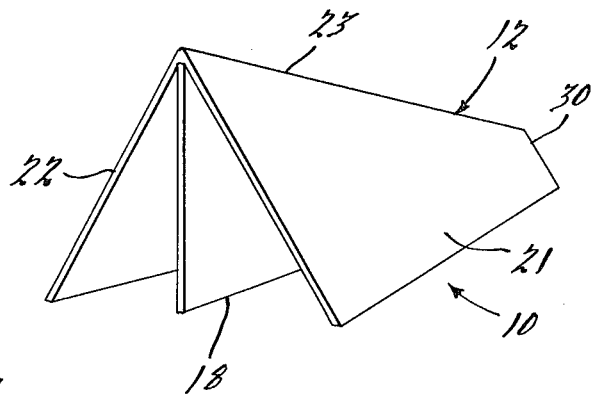
FIG. 1 is a diagramatic representation of the nasal pyramid.
Figure 2:
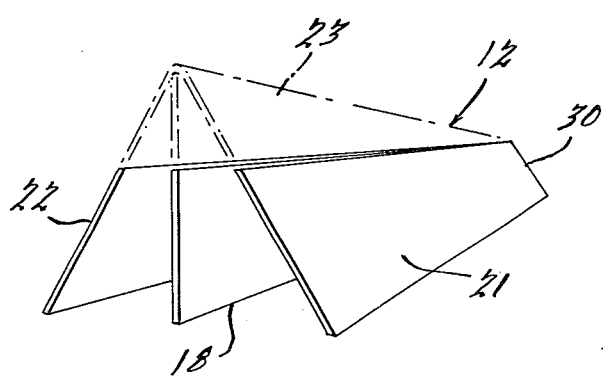
FIG. 2 is a diagramatic representation of the nasal pyramid subsequent to resection of the dorsum.
Figure 3:
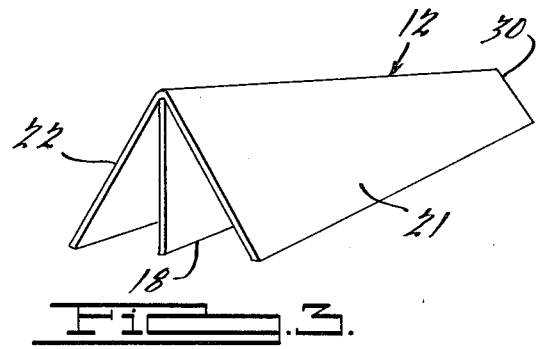
FIG. 3 is a diagramatic representation of the nasal pyramid after reformation.
Figure 4:
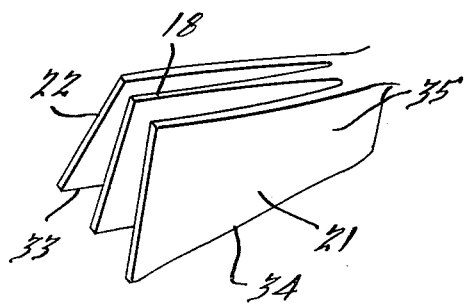
FIG. 4 is a view showing the resected dorsum and initial fracture line between the bony vault and the maxilla.
Figure 5:
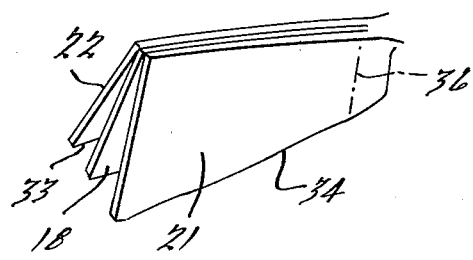
FIG. 5 is a view showing the desired fracture line of the cephalic segment.

As shown diagramatically in FIGS. 1–3, as well as in FIGS. 4 and 5, during rhinoplasty the dorsum 18 is resected, separating the dorsal edge 23 of the bony and cartilaginous vaults 12 and 14 from the walls thereof. Thereafter, the cartilaginous vaults 12 and 14 must rely on the remaining attachment to the nasal bones 21 and 22 for their support and lateral distraction. The change in the nasal pyramid 10 can be visualized by recognizing that the nasal pyramid 10 forms equilateral triangles of increasing size, the smallest being at the radix 30 and the largest at the caudal end of the nasal bones 21 and 22. Following dorsal resection, the loss of the dorsal edge 23 produces an open pyramid. In order to close the open pyramid as well as reconstruct a smaller pyramid, the nasal bones 21 and 22 must first be separated from the maxilla at their bases. Therefore, the nasal bones 21 and 22 are fractured to reform the nasal pyramid 10. The tool of the instant invention facilitates controlled fracture of the nasal bones 21 and 22.

Preferably the line of separation of the nasal bones 21 and 22 from their base follows the bases 33 and 34 thereof, leaving a narrow unfractured cephalic segment 35 in the area of the medial canthal ligament extending from the lateral osteotomy to the dorsum. It is this cephalic segment 35 that must be fractured, along a controlled line 36 extending from a point high in the nasion to a point above and anterior to the attachment of the medial canthal ligament as shown in FIGS. 5 and 8. Because bone continuity is important for a natural postoperative nasal contour, the fracture line 36 in the cephalic segment is preferably an undisplaced impacted fracture.

As best seen in FIG. 7, a surgical instrument 40 in accordance with the instant invention comprises what may be characterized as a forceps having scissor portions 44 and 46 joined to one another by a pivot pin 48. The scissor portions 44 and 46 have curved handles 50 and 52, respectively, that are normally biased apart by a spring 54. The scissor portion 44 has a relatively blunt nose or outer jaw portion 56, while the scissor portion 46 has a chisel edge inner jaw portion 58. In addition, the scissor portion 46 has an anvil 60 at the opposite end thereof from the chisel portion 58 to facilitate driving of the chisel edge of the jaw portion 58 into the bony structure above the septum to a position high in the nasion adjacent the radix 30 of the bony vault 12.

As best seen in FIG. 8, the chisel edge portion 58 of the scissor portion 46 is inserted lengthwise and parallel to the nasal bone 22 and tapped into position with the chisel edge thereof high in the nasion at the inside of the nasal bone 22, the blunt jaw portion 56 of the scissor portion 44 following along the outer wall of the nasal bone 22 with the flat inner sides of the jaws positioned to clamp the nasal bone therebetween as shown in FIG. 8.

As best seen in FIG. 9, the handle portions 52 and 50 of the instrument 40 are thereafter compressed towards one another against the bias of the spring 54 closing the nose 56 against the wall 22 of the bony vault 12 and chisel portion 58 of the instrument 40. Thereafter the instrument 40 is rotated clockwise, as seen in FIG. 9 of the drawings, to effect a controlled undisplaced impacted fracture of the wall 22 of the bony vault 12 parallel to the chisel edge of the jaw 58, thereby conditioning the "open pyramid" to be closed by "swinging" or moving the bone 22 towards the resected dorsum 18.

As best seen in FIG. 10, a modified embodiment of the instant invention comprises a tool 62 having scissor portions 64 and 66 joined to one another by a pivot pin 68. The scissor portions 64 and 66 have curved handles 70 and 72 that are normally biased apart as by a spring 74. The scissor portion 64 has a relatively blunt nose portion 76, with a pivoted pad 78 thereon, while the scissor portion 66 has a chisel edge 80 thereon. The scissor portion 66 has an anvil 82 at the opposite end of the chisel portion 80 to facilitate driving of the chisel edge into position adjacent the radix 30 of the bony vault 12.

The pad 78 is articulated relative to the nose portion 76 to insure that a firm even grip is obtained on the nasal bone 22 of the bony vault 12 upon rotation of the instrument 62 to effect fracture of the bone 22.

It is understood that the foregoing description is that of the preferred embodiment of the invention and that various changes and modifications may be made thereto without departing from the spirit and scope of the invention, as defined in the appended claims.

What is claimed is:

1. A special purpose forceps adapted primarily for use in rhinoplasty to produce a controlled infracture of the nasal bone precisely along a line extending from a point high in the nasion to a point above and anterior to the attachment of the medial canthal ligament comprising pivotally interconnected, essentially thin, elongate inner and outer jaws;

a pair of elongate handles each connected to a respective jaw and operative manually to move said jaws into and out of clamping engagement with each other, said inner and outer jaws adapted to be inserted lengthwise, parallel to, and at the inner and outer sides, respectively, of said nasal bone, said inner jaw having a transverse terminal end defining a straight-line chisel edge that is sufficiently sharp to be driven into and to penetrate the nasion to a point slightly above said proposed fracture line; and anvil means on the handle associated with said inner jaw for use in driving said chisel edge into the nasion, said anvil means, the pivot interconnecting said jaws, and said chisel edge being sufficiently in-line with each other so that hammer blows against said anvil means are transmitted to said chisel edge to drive the latter into the frontal process of the maxilla without significant lateral deviation of said edge, said jaws having mutually engageable clamping surfaces adjacent to the chisel edge of said inner jaw adapted to clamp said nasal bone therebetween, said chisel edge being of a length substantially equal to the width of said nasal bone at the proposed fracture line and said clamping surfaces being a width to engage said nasal bone for a substantial portion of its width near said proposed fracture line, whereby, when said nasal bone is clamped between said jaws and the forceps is manipulated to turn or pivot generally about said chisel edge and simultaneously to apply pressure longitudinally upwardly against said bone, a controlled infracture of the latter occurs parallel to said chisel edge without significant avulsion and tearing of the periosteum and muscle attachments in the area of the nasion.

2. A forceps according to claim 1, wherein the terminal portion of said inner jaw below said chisel edge is curved slightly laterally toward said outer jaw to conform generally to the lateral curve of the nasal bone in the area of the proposed infracture.

3. A forceps according to claim 1, wherein said inner jaw is at least as long as said outer jaw, and
wherein the clamping surface of said outer jaw is convexly curved adjacent to the tip of the jaw to define the area of contact with said inner jaw.

4. A forceps according to claim 1, wherein said inner jaw is longer than said outer jaw to position said chisel edge longitudinally beyond the tip of said outer jaw,
whereby said chisel edge is above and the tip of said outer jaw is below the medial canthal ligament when said chisel edge is driven to its final position in the nasion.

5. A forceps according to claim 1, wherein said outer jaw has inner and outer parts,
said inner part being pivotally mounted on said outer part at the inner side of the latter for rocking movement about an axis substantially parallel to said first-mentioned pivot connection,
said inner part defining the clamping surface of said outer jaw and being rockably adjustable in use to conform to the position of said inner jaw and the shape of the nasal bone being clamped.

* * * * *